United States Patent
Shinohara et al.

(10) Patent No.: US 7,689,266 B2
(45) Date of Patent: Mar. 30, 2010

(54) MEDICAL IMAGE DIAGNOSIS APPARATUS

(75) Inventors: Akiko Shinohara, Matsudo (JP); Shirou Oota, Matsudo (JP); Takashi Tsukizu, Nagareyama (JP)

(73) Assignee: Hitachi Medical Corporation, Tokyo (JP)

( * ) Notice: Subject to any disclaimer, the term of this patent is extended or adjusted under 35 U.S.C. 154(b) by 460 days.

(21) Appl. No.: 10/521,978
(22) PCT Filed: Jul. 22, 2003
(86) PCT No.: PCT/JP03/09239

§ 371 (c)(1),
(2), (4) Date: Jan. 21, 2005

(87) PCT Pub. No.: WO2004/008966

PCT Pub. Date: Jan. 29, 2004

(65) Prior Publication Data

US 2005/0245804 A1 Nov. 3, 2005

(30) Foreign Application Priority Data

Jul. 22, 2002 (JP) .............................. 2002-212482

(51) Int. Cl.
*A61B 6/02* (2006.01)
*A61B 6/03* (2006.01)
(52) U.S. Cl. .......................... 600/411; 378/4; 600/440; 600/407
(58) Field of Classification Search ................. 600/407, 600/436, 440, 411, 463; 340/721, 723; 345/173, 345/145; 433/24; 382/103, 180, 124, 128; 378/42, 1–20; 606/130
See application file for complete search history.

(56) References Cited

U.S. PATENT DOCUMENTS 4,642,621 A * 2/1987 Nemoto et al. .............. 345/634

(Continued)

FOREIGN PATENT DOCUMENTS

JP 5-317298 12/1993

(Continued)

OTHER PUBLICATIONS

Jun. 30, 2008 official action (and English translation thereof) in connection with a counterpart Japanese patent application No. 2002-212482.

*Primary Examiner*—Eric F Winakur
*Assistant Examiner*—Lawrence N Laryea
(74) *Attorney, Agent, or Firm*—Cooper & Dunham LLP (57) ABSTRACT

In a medical image diagnosis apparatus which forms a scanogram image of a subject and forms tomographic images under imaging conditions set by using the scanogram image, an imaging condition setting frame 33 independent of the scanogram image 31 is provided on a monitor 14. Desired imaging for which imaging conditions are to be set is designated by inputting a numeric value presenting an ordinal number for imaging in a numeric value input box 40 in the imaging condition setting frame 33. A pointer is set to a frame 41, a mark 42 or a dotted line 43 and dragged, thus enabling imaging conditions indicating the number of instances of imaging and image reconstruction and image reconstruction positions for the designated imaging. Settings in the imaging condition setting frame 33 are reflected in a frame 32A and lines 32B on the scanogram image 31 indicating the number of instances of imaging and image reconstruction and image reconstruction positions. In this way, the frame, lines and so on displayed on the scanogram image and indicating the imaging conditions for the desired imaging can be operated speedily and correctly.

16 Claims, 5 Drawing Sheets

U.S. PATENT DOCUMENTS

| | | | |
|---|---|---|---|
| 4,947,414 A * | 8/1990 | Stein | 378/55 |
| 5,371,778 A * | 12/1994 | Yanof et al. | 378/4 |
| 5,761,334 A * | 6/1998 | Nakajima et al. | 382/132 |
| 5,803,914 A * | 9/1998 | Ryals et al. | 600/407 |
| 5,883,933 A * | 3/1999 | Goto et al. | 378/62 |
| 6,063,032 A * | 5/2000 | Grunwald | 600/440 |
| 6,188,744 B1 | 2/2001 | Shinohara et al. | |
| 6,215,479 B1 * | 4/2001 | Matsui | 345/173 |
| 6,627,871 B2 * | 9/2003 | Iwamoto et al. | 250/221 |
| 6,632,089 B2 * | 10/2003 | Rubbert et al. | 433/24 |
| 6,894,707 B2 * | 5/2005 | Nemoto | 715/730 |
| 7,239,732 B1 * | 7/2007 | Yamada | 382/132 |
| 2003/0212327 A1 * | 11/2003 | Wang et al. | 600/437 |

FOREIGN PATENT DOCUMENTS

| | | |
|---|---|---|
| JP | 7-227391 | 8/1995 |
| JP | 7-275237 | 10/1995 |
| JP | 8-103440 | 4/1996 |
| JP | 8-289887 | 11/1996 |
| JP | 9-313476 | 12/1997 |
| JP | 10-52423 | 2/1998 |
| JP | 10-192272 | 7/1998 |
| JP | 11342125 | 12/1999 |
| JP | 2000-245727 | 9/2000 |
| JP | 2002-200072 | 7/2002 |

* cited by examiner

MEDICAL IMAGE DIAGNOSIS APPARATUS

TECHNICAL FIELD

The present invention relates to a medical image diagnosis apparatus and, more particularly, to a medical image diagnosis apparatus capable of setting imaging conditions such as an imaging position and range, a certain number of instances of image reconstruction, image reconstruction positions and a scanner angle when tomographic images are formed by using an image of the whole of a subject and a scanogram image of the subject in a case where medical images are formed by using a medical image diagnosis apparatus such as an X-ray CT apparatus or an MRI apparatus.

BACKGROUND ART

Figure 5:
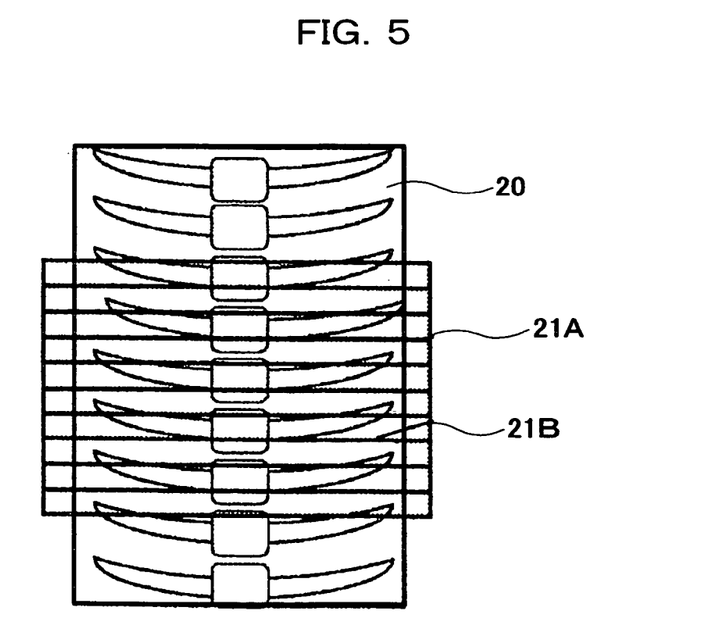
FIG. 5 is a diagram used for explanation of a conventional method of setting imaging conditions by using a scanogram image.

In a conventional technique, when an image of a desired portion of a subject is obtained by using a medical image diagnosis apparatus such as an X-ray CT apparatus or a magnetic resonance apparatus, an image of the whole of a subject or a fluoroscopic image (scanogram) of the subject is first formed along the body axis of the subject and a scanogram image 20 is displayed on a monitor, as shown in FIG. 5.

Figure 6:
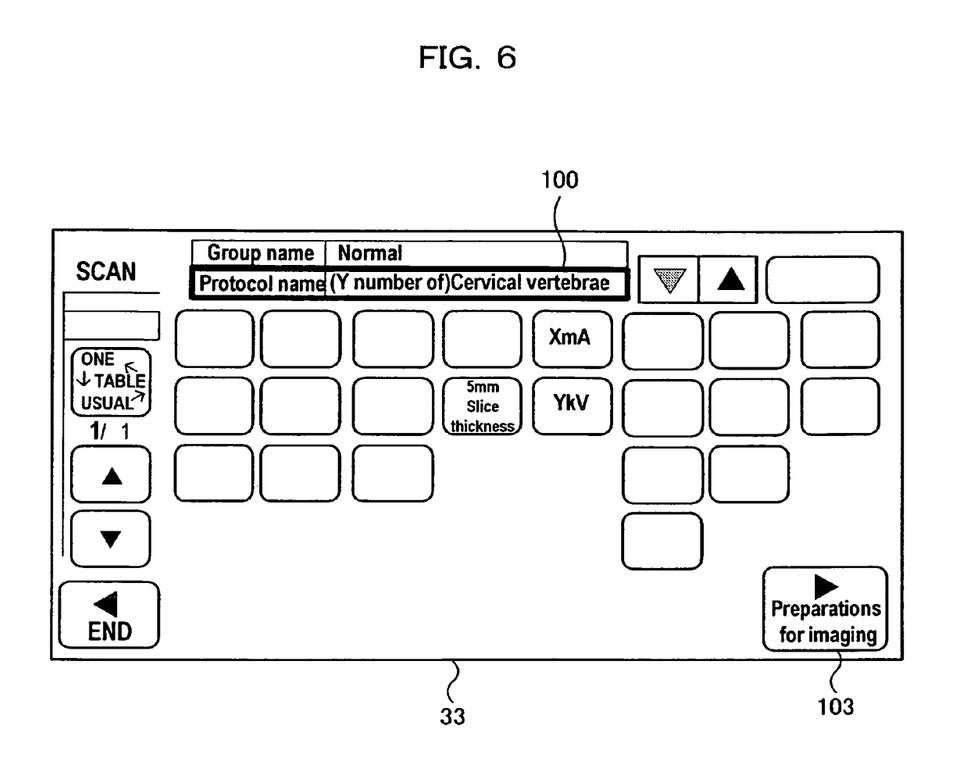
FIG. 6 is a diagram showing a conventional imaging condition setting frame.

In ordinary cases, an imaging condition setting frame for designating an imaging protocol and imaging conditions is separately provided in a window provided on a screen on which the scanogram image 20 is displayed or on a touch panel provided separately from the screen. Conditions for imaging are set in this frame. Ordinarily, depending on the position to be imaged, a list of frequently-used protocols registered in advance is shown, for example, from Protocol Name 100 shown in FIG. 6, and a required protocol in the list is selected. For example, when Protocol Name 100 in FIG. 6 is selected, a pull-down menu 101 shown in FIG. 7 appears. If a mark 102 corresponding to "(Y number of) cervical vertebrae" in the pull-down menu 101 is pointed, the corresponding protocol is selected and indicated in Protocol Name 100 in FIG. 6.

Figure 7:
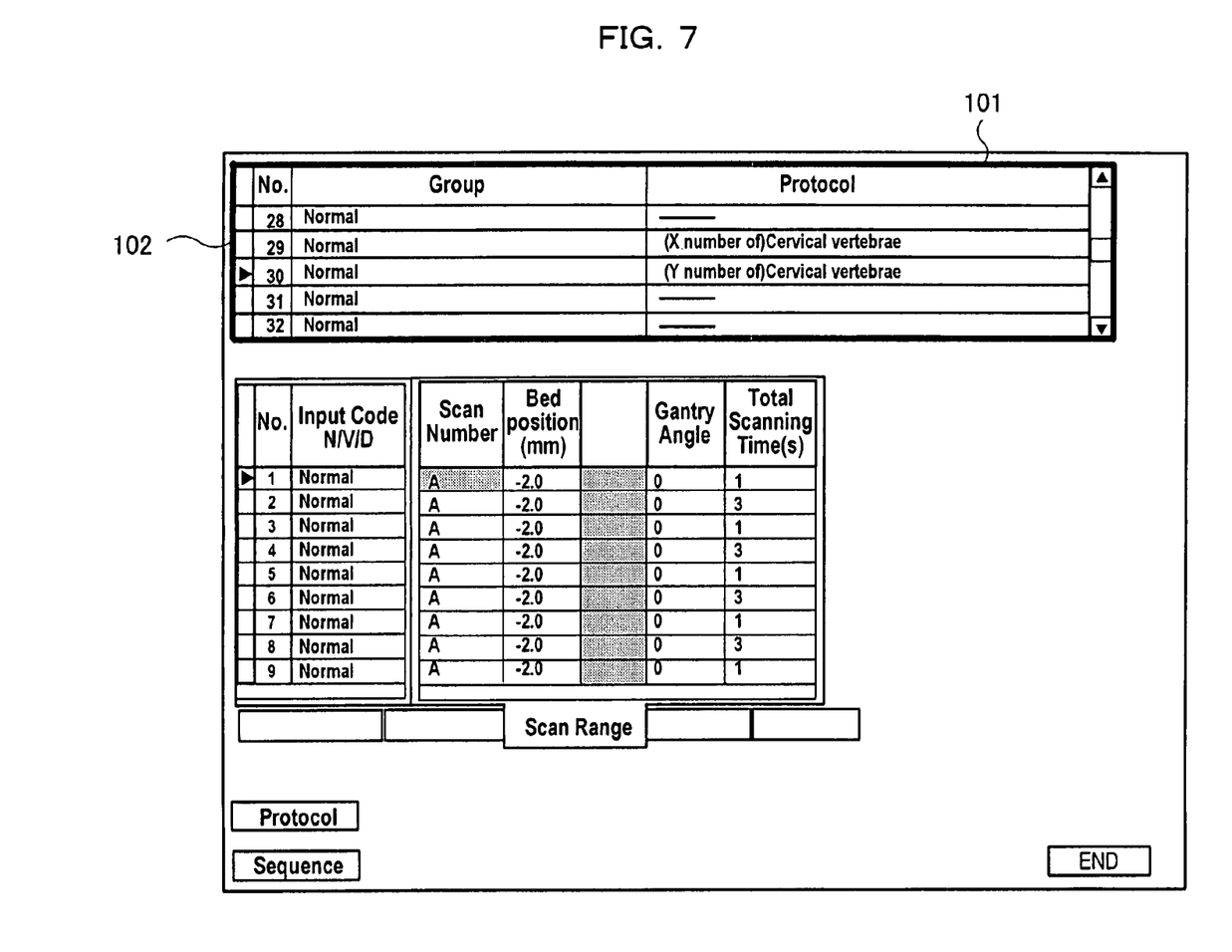
FIG. 7 is a diagram showing a pull-down menu which appears when a selection is made from protocols in the conventional imaging condition setting frame.

Protocols are displayed as shown in FIG. 7 to enable selection therefrom. After a protocol has been selected in this way, details of scan conditions may be changed. In such a case, a change is made by designating a selection button shown in FIG. 6. For example, the slice thickness can be changed to 5 mm by selecting "5 mm slice thickness". After imaging conditions have been determined as described above, an imaging preparation button 103 is pressed and a gantry thereby starts rotating. When steady rotation is attained, preparations for imaging are completed. If a start button is pressed after the completion of preparations for imaging, imaging is started by radiating X-rays according to the above-described imaging conditions.

When the above-described imaging conditions are input, a frame 21A indicating a scan area and a plurality of lines 21B indicating slice intervals are displayed according to the selected conditions, as shown in FIG. 5. Such imaging condition designation methods are disclosed in Japanese Patent Application Laid-Open Nos. 9-313476 and 8-103440.

In such a conventional medical image diagnosis apparatus, imaging conditions such as an imaging position and area, a certain number of instances of image reconstruction and image reconstruction positions can be changed by using the frame 21A and lines 21B. In a case where a certain number of instances of imaging and image reconstruction (scan area) is set such that the whole of an internal organ is covered, an external operating device such as a mouse is used for setting. More specifically, a pointer is set to the frame 21A and dragged to increase or reduce the size of the frame 21A, thereby changing the number of instances of imaging and image reconstruction. After imaging conditions have been set in the above-described manner, imaging of tomographic images is performed according to the set imaging conditions.

However, the frame and lines displayed on the scanogram image to indicate imaging conditions correspond to the actual scan area, imaging and image reconstruction positions and angle, and so on, and there is a problem described below. In a case where a plurality of imaging conditions (e.g., the condition for imaging of (Y number of) cervical vertebrae in the figure) is designated according to a protocol selection such as shown in FIG. 7 or in a case where imaging of one portion is performed a certain number of times (for example, in a case where imaging is performed before and after injection of a contrast medium), the frames and lines corresponding to imaging performed the certain number of times are displayed in a superposed state. When one of the frames, lines and so on corresponding to one of the imaging conditions which the operator wishes to change is directly operated with the mouse to change the imaging condition, there is a possibility of some of the other imaging lines, frames and so on existing at a nearby position being inadvertently operated.

There is another problem that a substantially long time is therefore required for setting of imaging conditions and the operation efficiency is reduced.

BRIEF SUMMARY

In an aspect of the present disclosure, a medical image diagnosis apparatus capable of speedily and correctly operating a frame, line or the like, representing a desired imaging condition is provided.

For example, a medical image diagnosis apparatus is provided which forms an image of the whole of a subject portion and forms a plurality of tomographic images under imaging conditions set with respect to the whole image, the medical image diagnosis apparatus comprising first display device of displaying the whole image, second display device of displaying an imaging condition setting frame for setting imaging conditions for imaging of a plurality of tomographic images with respect to each of a first imaging sequence, a second imaging sequence, . . . , imaging sequence designation device of designating a desired order of imaging for which the imaging conditions are set, operating device of setting imaging conditions at the time of imaging in the order designated by the sequence designation device on the imaging condition setting frame, and display control device of displaying information indicating the positions of imaging of the plurality of tomographic images on the whole image displayed on the first display device on the basis of the display conditions set by the operating device.

That is, in the case of an X-ray CT apparatus for example, the imaging condition setting frame for setting imaging conditions is displayed in a separate window on the display device on which a scanogram image is displayed or on another display device such as a touch panel. The imaging condition is, for example, a certain number of instances of imaging and image reconstruction, positions of imaging and image reconstruction. In this independent imaging condition setting frame, a desired one of instances of imaging can be designated by an operation through an external operating device, and imaging conditions for the designated imaging can be individually set by operations through the external operating device. For example, in a case where a plurality of imaging sequences are performed, when a change is made in the imaging conditions for the first imaging sequence, the first imaging sequence is designated and the imaging conditions related to the first imaging sequence are set. The imaging condition setting in this case does not influence the imaging conditions for the imaging sequences other than the first imaging sequence. A plurality of imaging sequences can be simultaneously set. In this case, the same imaging conditions are set with respect to the plurality of imaging sequences designated.

The imaging conditions set in this way are reflected in display of the frame, lines and the like which indicate the imaging conditions, being displayed on the scanogram. Thus, not direct operations on the frame and lines displayed on the scanogram image with a mouse or the like but designation of the desired imaging on the imaging condition setting frame independent of the scanogram image is performed. Therefore, it is possible to avoid occurrence of an erroneous operation on some of frames, lines or the like existing at the same position but not to be operated. Moreover, it is possible to set desired imaging conditions speedily and correctly with respect to the designated imaging.

BEST MODE FOR CARRYING OUT THE INVENTION

A preferred embodiment of a medical image diagnosis apparatus in accordance with the present invention will be described in detail with reference to the accompanying drawings.

Figure 1:
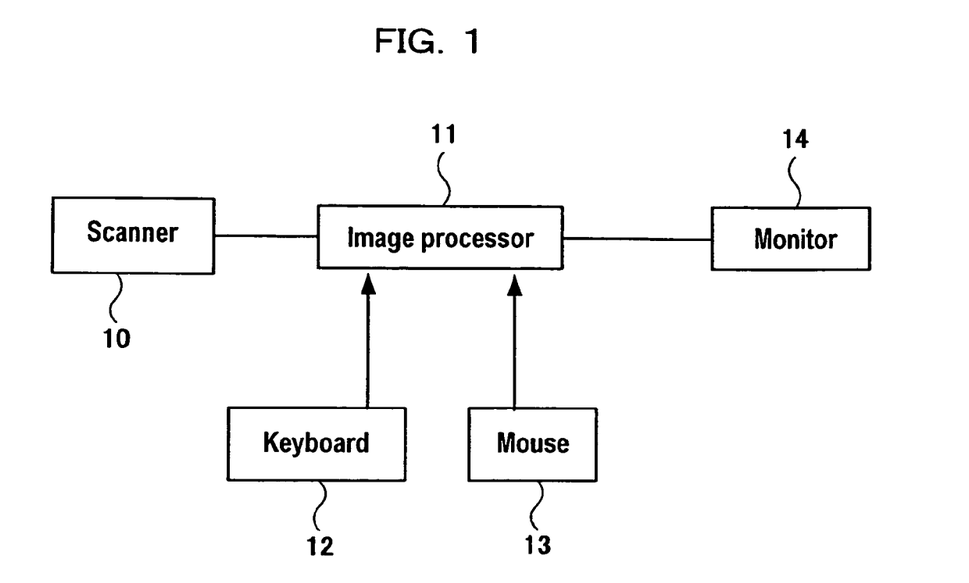
FIG. 1 is a hardware configuration diagram showing an embodiment of a medical image diagnosis apparatus in accordance with the present invention.

FIG. 1 is a hardware configuration diagram showing an embodiment of a medical image diagnosis apparatus in accordance with the present invention.

The medical image diagnosis apparatus shown in FIG. 1 is, for example, an X-ray CT apparatus constituted by a scanner 10 which forms a scanogram image or a tomographic image of a subject, an image processor 11 having a central processing unit which performs overall control of the apparatus, an image reconstruction processing circuit which executes image reconstruction calculation, and a magnetic disk or the like on which a program for realizing imaging condition setting in accordance with the present invention, tomographic images, etc., are stored, a keyboard 12 provided as an external operating device, a pointing device 13 (which will be described as a mouse by way of example, but which may be any other pointing device such as a trackball, a trackpad, a keyboard or a touch panel) and a monitor 14.

In a gantry of the scanner 10, an X-ray tube and an X-ray detector are placed in such a positional relationship as to face each other. X-rays generated from the X-ray tube pass through a subject lying on a bed to be detected by the X-ray detector. The X-rays are converted into an electrical signal by the X-ray detector and the signal is sent to the image processor 11.

The image processor 11 reconstructs a tomographic image by a well-known method from data input by measurement with the scanner. The reconstructed tomographic image is displayed on the monitor 14 and is stored on the magnetic disk for redisplay for example.

Figure 2:
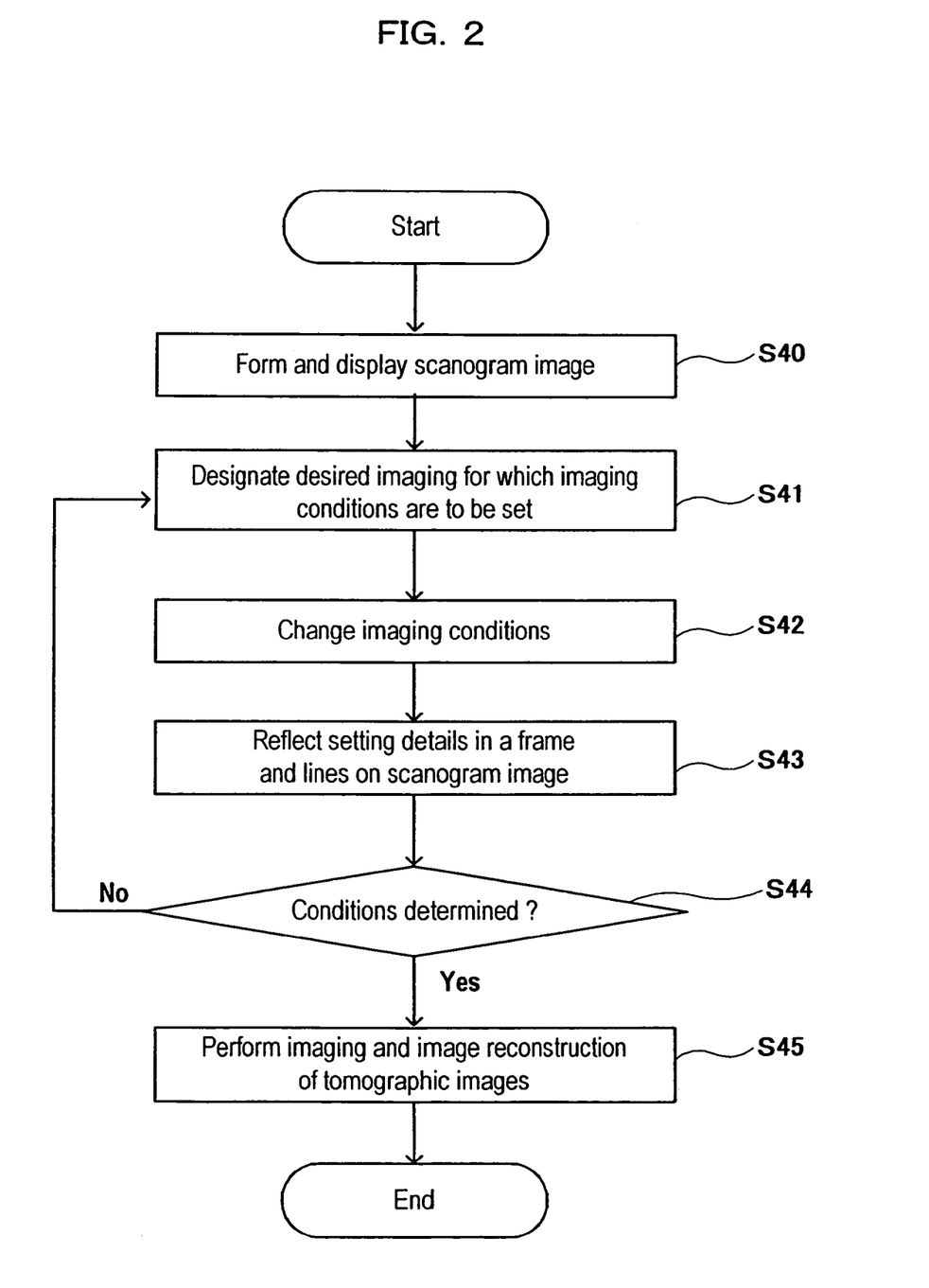
FIG. 2 is a flowchart used for explanation of an imaging condition setting procedure in accordance with the present invention.

An imaging condition setting procedure (software for realizing imaging condition setting) in the present invention will now be described with reference to FIG. 2.

Before imaging for the above-mentioned tomographic image, a scanogram image is formed for the purpose of setting imaging conditions including the number of instances of subject imaging and image reconstruction and positions of imaging and image reconstruction, and the scanogram image is displayed on the monitor 14 (step S40).

The scanogram image is an X-ray image first formed for correct imaging of an area covering a target organ by irradiating the subject with X-rays while moving only the bed on which the subject is laid, or only the gantry having the X-ray tube and the X-ray detector, without rotating the X-ray tube and the X-ray detector.

Figure 3:
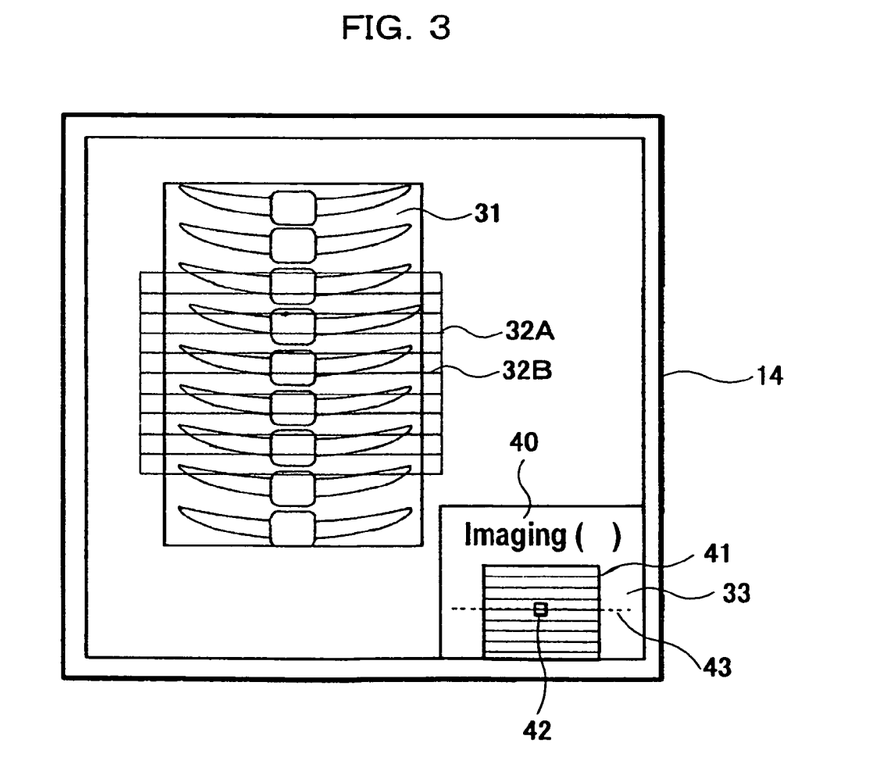
FIG. 3 is a diagram used for explanation of the present invention, showing an example of a screenful of image on a monitor in which an obtained scanogram image, etc., are displayed.

FIG. 3 shows an example of a screenful of image on the monitor, in which the obtained scanogram image, etc., are displayed.

As shown in FIG. 3, a frame 32A indicating a scan area and lines 32B indicating imaging and image reconstruction positions of tomographic images are displayed on the monitor 14 together with the scanogram image 31. An imaging condition setting frame 33, which is an operating image frame for setting imaging conditions, is also displayed in a window on the monitor 14 separately from the scanogram image or on a display device separately provided, as described above with respect to the conventional art.

The operator of the X-ray CT apparatus designates desired imaging with imaging condition settings on the imaging condition setting frame 33 (step S41). Imaging may be performed a certain number of times. For example, imaging may be performed before and after injection of a contrast medium or different organs may be imaged separately from each other. The desired imaging in such a case (first imaging, second imaging, and so on) is designated in a box 40.

Subsequently, imaging conditions such as an imaging position, an imaging area, a certain number of instances of image reconstruction and image reconstruction positions are set on the imaging condition setting frame 33 by using the external operating device, e.g., the mouse 13 or the keyboard 12 (step S42). If certain imaging condition has been set by selection of a protocol as described above with respect to the conventional art, and if this imaging condition is changed, a suitable operation is performed in step S42. This operation will be described below in detail.

Imaging conditions set on the imaging condition setting frame 33 are reflected via the CPU in the frame 32A, lines 32B and so on displayed on the scanogram image 31 (step S43). In a case where imaging conditions are displayed in separate display device, they are reflected by communication between CPUs respectively provided for the display device.

Processing from step S41 to step S43 is repeated until the imaging conditions for instances of imaging are determined by the operator of the X-ray CT apparatus (step S44). When imaging conditions for instances of imaging are determined, the image processor 11 performs imaging and image reconstruction of tomographic images (step S45).

Thus, imaging conditions set by using the independent imaging condition setting frame 33 are immediately reflected in the rectangular frame 32A displayed on the scanogram image 31, the lines 32B dividing the frame and so on. Therefore, desired imaging conditions can be easily set while checking the frame 32A, the lines 32B and so on.

The arrangement may be such that the above-described imaging conditions can be set by directly pointing the rectangular frame 32A and the lines 32B on the scanogram image 31.

Figure 4:
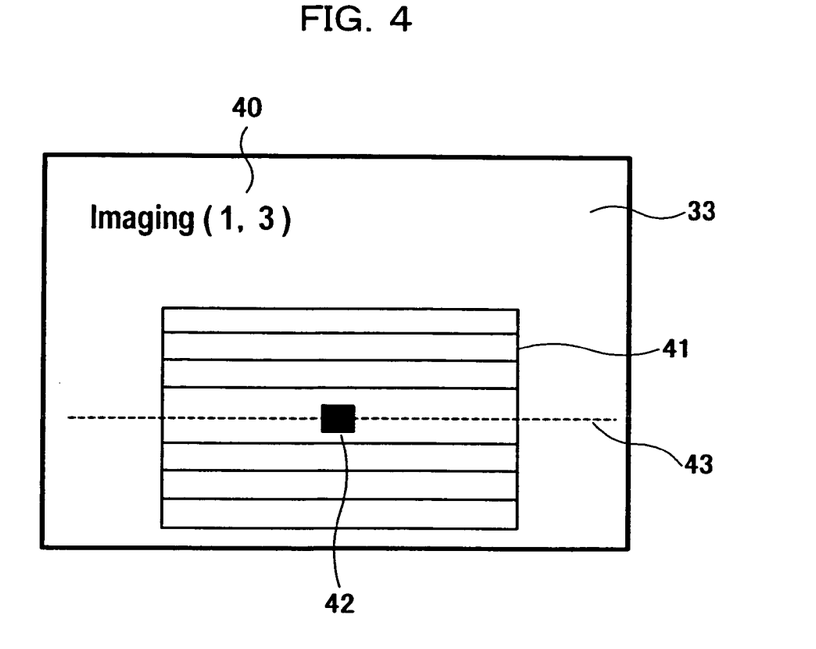
FIG. 4 is an enlarged diagram corresponding to the imaging condition setting frame shown in FIG. 3.

Concrete examples of setting of the above-described imaging conditions will be described with reference to FIG. 4. FIG. 4 is an enlarged diagram corresponding to the imaging condition setting frame 33 shown in FIG. 3.

<Example 1 Of Setting: An Example of Designation of a Desired Imaging Sequence for Which Imaging Conditions are Set>

A desired imaging sequence for which imaging conditions should be set is designated by using the external operating device, e.g., the mouse or the keyboard.

For example, in a case where the numeric value input body 40 is provided in the imaging condition setting frame 33 to enable designation of a desired imaging sequence, a numeric value corresponding to the ordinal number for a desired imaging sequence is input to the numeric value input box 40 to designate the desired imaging sequence. In the example shown in FIG. 4, numeric values "1" and "3" are input to the numeric value input box 40 to designate the first imaging sequence and the third imaging sequence.

<Example 2 Of Setting: An Example of Changing Image Reconstruction Positions and the Number of Instances of Image Reconstruction>

Image reconstruction conditions are changed by using the external operating device, e.g., the mouse or the keyboard.

For example, in a case where the number of instances of image reconstruction is changed by using the mouse or image reconstruction cross-sections are changed by using the mouse, the pointer (not shown) is set to the upper side or the lower side of a rectangular imaging condition setting frame 41 shown in the imaging condition setting frame 33, and the selected side is moved upward or downward by being dragged. By this operation, the vertical size of the rectangular frame 32A on the scanogram image 31 indicating imaging conditions set with respect to the imaging designated in Example 1 of setting is changed. According to the size changed by the operation, the number of lines 32B parallel to one pair of sides of the rectangular frame 32A and dividing the rectangular frame 32A is changed. Thus, the number of instances of imaging and image reconstruction are set. The rectangular frame 32A and the lines 32B parallel to one pair of sides of the rectangular frame 32A and dividing the rectangular frame 32A can be separately enlarged, reduced, added, deleted or moved. In Example 1 of setting, the number instances of imaging and image reconstruction in the first imaging sequence and the third imaging sequence are simultaneously set since the first imaging sequence and the third imaging sequence are set.

Example 3 Of Setting: An Example of Changing the Imaging Area and the Effective Field of View (F.O.V.) for Image Reconstruction>

The imaging area and the effective field of view (F.O.V.) for image reconstruction are changed by using the external operating device, e.g., the mouse or the keyboard.

For example, in a case where the effective field of view (F.O.V.) is changed by using the mouse, the pointer is set to the right side or the left side of the rectangular imaging condition setting frame 41 displayed in the imaging condition setting frame 33, and the selected side is moved to the left or right by being dragged. By this operation, the horizontal size of the rectangular frame 32A on the scanogram image 31 indicating imaging conditions set with respect to the imaging designated in Example 1 of setting is changed to increase or reduce the effective field of view (F.O.V.), thus setting the effective field of view (F.O.V.).

<Example 4 Of Setting: An Example of Changing the Imaging Position and the Image Reconstruction Position>

The imaging position and the image reconstruction positions are changed by using the external operating device, e.g., the mouse or the keyboard.

For example, in a case where the imaging position and the image reconstruction positions are changed by using the mouse, the pointer is set to a mark 42 displayed in the imaging condition setting frame 33, and the mark 42 is moved upward or downward or to the left or right by being dragged. By this operation, the positions of the rectangular frame 32A and the division lines 32B on the scanogram image 31 indicating imaging conditions set with respect to the imaging designated in Example 1 of setting are changed as a whole. Thus, the imaging position and the image reconstruction positions are set.

<Example 5 Of Setting: An Example of Changing the Imaging Angle and the Image Reconstruction Angle>

The imaging angle and the image reconstruction angle are changed by using the external operating device, e.g., the mouse or the keyboard.

For example, in a case where the imaging angle and the image reconstruction angle are changed by using the mouse, the pointer is set to one end of a dotted line 43 displayed in the imaging condition setting frame 33 and the end of the dotted line 43 is dragged upward or downward to tilt the dotted light 43 rightward or leftward about the mark 42. By this operation, the angle of the rectangular frame 32A and the division lines 32B on the scanogram image 31 indicating imaging conditions set with respect to the imaging designated in Example 1 of setting is changed as a whole. Thus, the imaging angle and the image reconstruction angle are set. In this way, the scanner angle (tilt angle) of the scanner 10 can be set. At this time, the external configuration of the rectangular frame becomes a parallelogram.

Needless to say, imaging designation described with respect to Example 1 of setting is performed before settings corresponding to Examples 2 to 5 of setting. The imaging condition setting frame 41 displayed in the imaging condition setting frame 33 shown in FIG. 4 is not limited to that similar to the rectangular frame 32A and the division lines 32B on the scanogram image 31 indicating imaging conditions. A move or a copy from the scanogram image 31 to the imaging condition setting frame 33, in the reverse direction or in mutual action may be made. The configuration relationship in such a case may be identity, similarly or analogy. That is, enabling a desired imaging condition to be set by observing the frame 32A and the lines 32B on the scanogram image 31 indicating imaging conditions and by using the other image frame (imaging condition setting frame 33) may suffice.

The imaging condition setting frame 33 is not limited to the case of being displayed in a picture-in-picture manner on the monitor 14 on which the scanogram image 31 is displayed. The imaging condition setting frame 33 may be displayed on another monitor. Further, while the present embodiment has been described as an X-ray CT apparatus by way of example, the present invention can be applied to setting of imaging conditions in other medical image diagnosis apparatus, e.g., an MRI apparatus.

INDUSTRIAL APPLICABILITY

According to the present invention, as described above, an imaging condition setting frame for setting imaging conditions such as an imaging position and area, a certain number of instances of image reconstruction, image reconstruction positions and a scan angle is provided separately from a display unit for displaying the entire image; a desired one of imaging sequences can be designated by using the imaging condition setting frame; imaging conditions relating to the designated imaging sequence can be individually set; and details of the setting are reflected in a rectangular frame and lines displayed on the scanogram image and indicating imaging conditions. Therefore, occurrence of an erroneous operation on some of frames, lines or the like existing at the same position but not to be operated can be avoided and desired imaging conditions can be set speedily and correctly with respect to the designated imaging.

The invention claimed is:

1. A medical image diagnosis apparatus which images a subject by forming a whole image of a subject portion of the subject, displays imaging conditions on the whole image, and allows an operator to set or modify the imaging conditions for imaging a tomographic image, the medical image diagnosis apparatus comprising:
   a first display device for displaying the whole image and the imaging conditions including a frame indicating a scan area and lines indicating imaging positions of tomographic images and image reconstruction positions of the tomographic images;
   a second display device;
   a display control device configured to extract one or more of the imaging conditions including the frame and the lines and control the second display device to display the extracted imaging conditions for imaging the tomographic images; and
   an operating device for setting or changing the imaging conditions for imaging the tomographic images, by adjusting the frame and the lines displayed by the second display device.

2. The medical image diagnosis apparatus according to claim 1, wherein the imaging conditions displayed on the first and second display device are imaging conditions displayed by graphic display and including at least one of an imaging position, an imaging area, a certain number of instances of image reconstruction, an image reconstruction position and a scanner angle.

3. The medical image diagnosis apparatus according to claim 2, wherein the imaging position and the imaging area in the imaging conditions are indicated by a rectangular frame and a mark in the rectangular frame in the first display device and the second display device, and are set in at least one of the first display device and the second display device.

4. The medical image diagnosis apparatus according to claim 3, wherein the number of instances of image reconstruction and the image reconstruction positions in the imaging conditions are indicated by lines provided in the rectangular frame and dividing the rectangular frame by extending parallel to sides of the rectangular frame, and are set in at least one of the first display device and the second display device.

5. The medical image diagnosis apparatus according to claim 4, wherein the operating device is configured to generate the division lines in the rectangular frame at any position and move the division lines to any position.

6. The medical image diagnosis apparatus according to claim 3, wherein the operating device is configured to extend or contract the rectangular frame in any direction, and move the mark to any position together with the rectangular frame.

7. The medical image diagnosis apparatus according to claim 3, wherein the operating device is configured to form a parallelogram by tilting the rectangular frame indicated in the first display device and the second display device, and set the scanner angle in the imaging conditions as the tilt angle of the parallelogram in the first display device and the second display device.

8. The medical image diagnosis apparatus according to any one of claims 3, to 7, wherein the operating device is configured to move or copy the rectangular frame, the division lines and the mark from the first display device to the second display device or between the first display device and the second display device in an identical, similar or analogous form.

9. The medical image diagnosis apparatus according to claim 1, wherein a display frame on the first display device and the display frame on the second display device share one monitoring screen.

10. The medical image diagnosis apparatus according to claim 1, wherein the imaging conditions displayed on the second display device further include imaging sequence ordinal numbers for setting the imaging conditions with respect to each of a plurality of imaging sequences.

11. The medical image diagnosis apparatus according to claim 10, wherein at least one of the imaging conditions for imaging varies among the imaging sequences.

12. The medical image diagnosis apparatus according to claim 10, wherein the desired order of execution of the plurality of imaging sequences is designated by inputting numeric values.

13. The medical image diagnosis apparatus according to any one of claims 1 to 10, wherein the second display device comprises a touch panel.

14. The medical image diagnosis apparatus according to any one of claims 9 to 7, wherein the operating device comprises a pointer.

15. The medical image diagnosis apparatus according to claim 1, wherein display devices for the first display device and the second display device are provided separately from each other.

16. A medical image diagnosis apparatus which forms a whole image of a subject portion of a subject and obtains one or more tomographic images under imaging conditions for imaging a tomographic image, the medical image diagnosis apparatus comprising:
   a first display device for displaying the whole image of the subject portion and the imaging conditions including a frame indicating a scan area and lines indicating imaging positions of the tomographic images and image reconstruction positions of the tomographic images;
   a second display device;
   a display control device configured to extract one or more of the imaging conditions including the frame and the lines and control the second display device to display the imaging conditions including the frame and the lines extracted from the first display device for setting the imaging conditions for obtaining the one or more tomographic images; and an operating device for an operator to selectively set the imaging conditions for imaging the tomographic images, by adjusting the frame and the lines displayed by said second display device, wherein said display control device controls the first display device to display, on the whole image, information indicating positions of said one or more tomographic images to be obtained based on the imaging conditions set with the operating device.

* * * * *